United States Patent [19]

Grodecki et al.

[11] Patent Number: 5,045,070
[45] Date of Patent: Sep. 3, 1991

[54] BODY CAVITY PROBE WITH EVERTING TUBE

[75] Inventors: Richard Grodecki, Milton; Raymond Laborie, St. Bruno, both of Canada

[73] Assignee: Pentotech, Ltd., Ontario, Canada

[21] Appl. No.: 288,136

[22] Filed: Dec. 22, 1988

[51] Int. Cl.$^5$ .............................................. A61M 5/00
[52] U.S. Cl. ..................................... 604/271; 604/165
[58] Field of Search ................. 604/271, 43, 264, 268, 604/96, 104, 164, 165

[56] References Cited

U.S. PATENT DOCUMENTS

| | | | |
|---|---|---|---|
| 3,500,819 | 3/1970 | Silverman | 604/271 |
| 4,321,915 | 3/1982 | Leighton et al. | 604/271 |
| 4,863,424 | 9/1989 | Blake, III et al. | 604/271 |
| 4,871,358 | 10/1989 | Gold | 604/271 |

*Primary Examiner*—C. Fred Rosenbaum
*Assistant Examiner*—Kathleen A. Daley
*Attorney, Agent, or Firm*—Sherman and Shalloway

[57] ABSTRACT

The present invention relates to a body cavity probe with an everting tube designed to ease insertion of the probe into the body cavity. The device includes the provision of a flexible introduction device mounted on the exterior of the tube and designed to be used to ease insertion of the probe into a body cavity. In a further aspect, the inventive probe may include a barrier designed to isolate the exterior of the body cavity from interior portions thereof. In a further aspect, a flexible accessory channel may be provided on the exterior of the device to permit entry into the body cavity from a different location. One preferred application of the teachings of the present invention is in the field of Urodynamics.

5 Claims, 2 Drawing Sheets

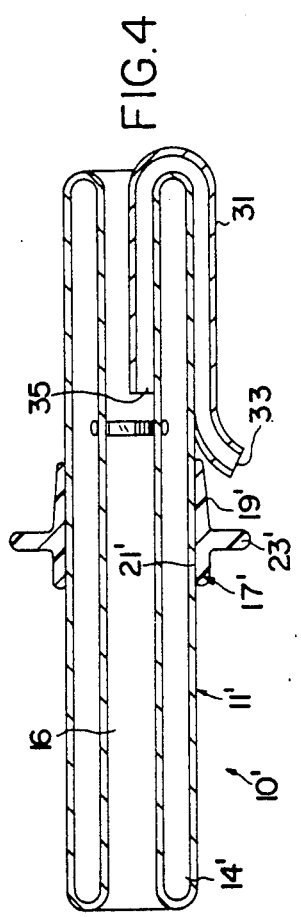
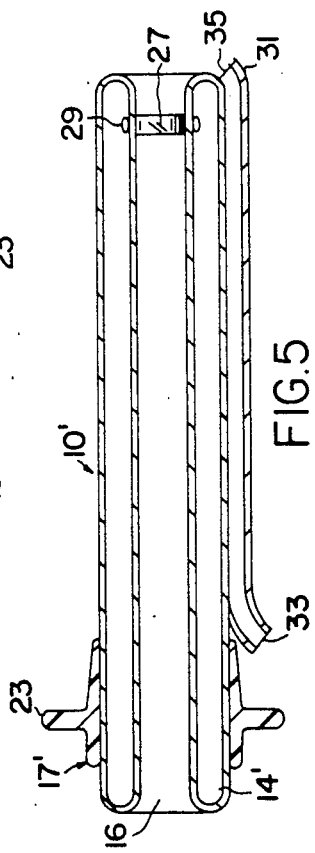
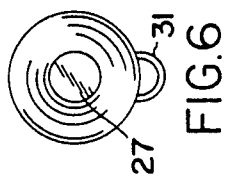
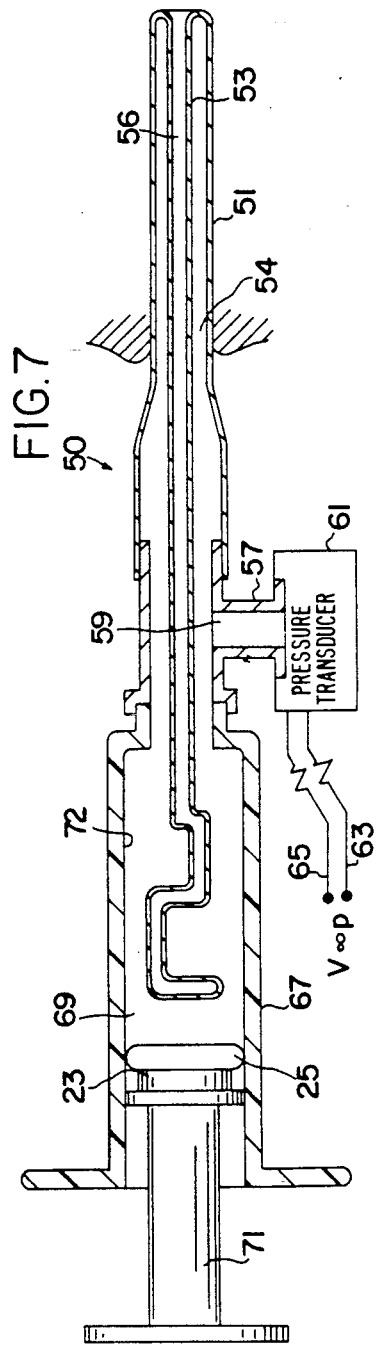

BODY CAVITY PROBE WITH EVERTING TUBE

BACKGROUND OF THE INVENTION

The present invention relates to a body cavity probe with everting tube. Generally speaking, body cavity probes with everting tubes are known, as will be demonstrated by the references discussed hereinbelow. However, to this time, no one has developed a probe with everting tube which combines ease of insertion into a body cavity with separation of the interior of the body cavity from an exterior probe. The following prior art is known to Applicant:

Publication titled "Hydraulic Systems Based On Topological Transformations of Flexible Envelopes, and Their Possible Application in Physiology and Medicine", H. Zeimer, et al., August, 1964, National Physical Laboratory of Israel, discloses various aspects of an everting tube. The everting tube, in one aspect, is connectable to a source of pressure. The everting tube is closed at its distal end by a plug. There is no teaching or suggestion in this publication that the plug is transparent. The teachings of this publication are believed to be of only general interest to the teachings of the present invention.

Publication titled "Toposcopy: Frictionless Method Entering Body Cavities and Tracts", Harry Zeimer, et al., July 15, 1966, *New York State Journal of Medicine*, discloses the use of an everting tube to enter body cavities and tracts, is no more pertinent than the Zeimer, et al., publication discussed above.

Publication titled "Toposcopic Catheter: A Design for Maneuvering Through Tortuous Vessels", John L. Doppman, M.D., et al., *Radiology*, September, 1979, discloses the use of an everting tube in conjunction with a catheter for entering body cavities. Again, there is no teaching or suggestion in this publication of the use of a flexible introduction device or a clear barrier. As such, this publication is believed to be of only general interest concerning the teachings of the present invention.

Publication titled "A Miniature Toposcopic Catheter Suitable for Small Diameter Tortuous Blood Vessels", Seth Goldstein, et al., *Toposcopy*, December, 1979, appears to disclose the same structure disclosed in the Doppman, et al., publication discussed above.

Publication titled "A Miniature Toposcopic Catheter Suitable for Small Diameter Tortuous Blood Vessels", S. R. Goldstein, et al., *Journal of Biomedical Engineering*, August, 1980, appears to disclose the same structure as the Doppman, et al., and Goldstein, et al., publications discussed above. The disclosure in this application at FIGS. 3 and 4 thereof of the construction of a toposcopic catheter and the schematic diagram of pressure and flow control systems therefor is believed only generally related to the teachings of the present invention.

A further disclosure of generally the same toposcopic catheter is found in a publication titled "The Toposcopic Catheter and the Fiber Optic pH Probe-Two Medical Instruments of Potential Use to Gastroenterologists", *Gastrointestinal Endoscocy*, Vol. 29, No. 3, 1983. This publication discloses the use of fiber optics in conjunction with the toposcopic catheter.

Publication titled "Toposcopic Catheter Traverses Narrow Vessels", *Journal of the American Medical Association*, Sept. 7, 1984, discusses the same structure set forth in the above discussed publications and is no more pertinent than their disclosures.

Publication titled "Everting (Toposcopic) Catheter for Broad Clinical Application", D. R. Shook, et al., *Transactions of the A.S.M.E.*, May, 1986, is a further publication discussing the same catheter discussed in the above discussed publications. For example, FIG. 2 of this publication is related to the Figure on page 1109 of the publication from the *Journal of the American Medical Association*. While this publication also discloses flow mechanics in the use of an everting tube, this aspect is believed to be of only general relation to the teachings of the present invention.

Publication titled "The Ins and Outs of Toposcopy and the Everting Catheter", Daniel R. Shook, *SOMA*, July, 1987, traces the history of the use of the everting catheter through many of the publications discussed hereinabove and includes copies of drawings and Figures which are first disclosed in the above listed and discussed publications.

U.S. Pat. No. 3,168,092 to Silverman discloses a medical probing instrument having flexible, extrudable tubing adapted to be extroverted under pressure into a body cavity. While Silverman shows the use of an optical instrument in conjunction with the flexible tubing, which optical instrument has lenses 45 and 47, Silverman fails to teach the concept of incorporating a clear barrier into the flexible tubing itself, as taught by the present invention.

U.S. Pat. No. 3,506,011 to Silverman discloses a medical instrument for everting a thinwalled flexible tubing which, as best seen in FIGS. 11 and 12 thereof may have associated therewith a conical fitting having a plurality of circumferentially-spaced longitudinal splits allowing flexibility. The conical fitting is provided to allow easy insertion of the device into a body cavity, with the splits allowing expansion of the fitting to allow the flexible tubing to pass therepast. This is different from the teachings of the present invention which contemplates the use of a flexible introduction device which is connected to the outer well of the flexible tube and which preferably uses inherent flexibility rather than longitudinal splits to facilitate insertion of the flexible tube and subsequent advancement thereof.

U.S. Pat. No. 4,007,610 to Masuda discloses a method and apparatus for passing an article through an interior of a pipe. The device taught by Masuda is believed to be only generally related to the teachings of the present invention.

U.S. Pat. No. 4,321,915 to Leighton, et al., discloses a device for everting a tube which includes a valve controlling either admission of pressure or evacuation through vacuum source to move the everting tube device. A fiber optic bundle is utilized and advanced by movements of the everting tube. This patent is believed to be only generally related to the teachings of the present invention.

U.S. Pat. No. 4,437,857 to Goldstein, et al., discloses a device which is disclosed in a number of the publications listed above, including those to Doppman, et al., Jones, et al., Goldstein, et al., and Shook, et al.

U.S. Pat. No. 4,530,698 to Goldstein, et al., matured from an application which was a divisional of the application from which matured U.S. Pat. No. 4,437,857.

U.S. Pat. No. 4,615,331 to Kramann discloses a medical instrument with aid to introduction, including the use of an everting tube having a plurality of folds upon itself which telescope as the tube advanced. This teaching is believed to be only generally related to the teachings of the present invention.

German Offenlegungsschrift 2,406,823 discloses the use of an everting tube which is advanced and retracted through the use of fluid pressure. This patent discloses, in FIG. 2, the use of telescoping tube structure similar to that which is disclosed in U.S. Pat. No. 4,615,331 to Kramann.

SUMMARY OF THE INVENTION

The present invention relates to a body cavity probe with everting tube. As should be clear from the discussion of prior art known to Applicant set forth above, the basic concept of the use of an everting tube to allow easy entry into a body cavity is old per se. However, it should be equally clear from the above discussion that the prior art is lacking in the respect of failing to provide for the easy insertion of such an everting tube system, and as failing to provide a safe way to use an everting tube system to examine the interior of a body cavity while completely isolating the viewer from internal body cavity fluids. As horror stories concerning the contracting of AIDS by physicians examining their patients multiply, a need has developed for a device which may be used to examine body cavities while isolating the examining physician from body fluids which could transmit diseases, including AIDS.

The present invention includes the following aspects and features:

(a) In a first aspect, the present invention includes an everting flexible tube which is elongated in the longitudinal direction and preferably includes inner and outer annular walls which are integral with one another to allow advancement of one wall with respect to another wall which may be held stationary, as desired.

(b) Attached to the outer wall is a flexible introduction device which includes a radially outwardly-extending projection designed to be gripped by the user, a rearward-facing portion attached to the projection and lying against and attached to the outer wall of the everting tube, and a forward-facing portion connected to the rearward-facing portion and the projection but unattached to the everting tube so that the tube may be everted to a position wherein the forward-facing portion extends outwardly beyond the forward extension of the everting tube.

(c) The forward-facing portion described above is preferably formed of a shape such that, in its relaxed condition, it converges in the forward-facing direction. This structure is provided to allow easy access to body cavities through insertion of the forward-facing portion therein and thereafter everting the tube through the forward-facing portion and into the body cavity. While the forward-facing portion is flexible, it is designed to have more rigidity than the everting tube and greater thickness to allow easy insertion into a body cavity. However, after the forward-facing portion has been inserted into the body cavity, when the tube is everted through the forward-facing portion, the fluid pressure within the everted tube is sufficiently great enough to stretch the forward-facing portion of the flexible introduction device to allow the everting tube to safely extend therethrough.

(d) In a further aspect, a clear barrier device may be incorporated into the invention on the inner wall thereof, such that, after the tube has been everted, by insertion of an inspection device and advancement thereof, to a position with the clear barrier device inserted into the body cavity, the inspection device, such as a viewing device or the like, will allow viewing of the internal structure of the body cavity without direct exposure to internal body fluids, such as those which may transmit diseases.

(e) In a further aspect, an accessory channel may be attached to the exterior walls of the everting tube for the purpose of allowing the passage into the body cavity of instruments or other devices after the everting tube has been everted to a position wherein it has been inserted into the body cavity.

(f) In a further aspect, the inventive everting tube may be utilized in a urodynamics application wherein flows and pressures in the urinary tract may be examined. In this aspect, the tube may be everted into the urinary tract by continuous application of pressure while a pressure transducer monitors any pressure fluctuations within the chamber of the everting tube. Such pressure fluctuations may be interpreted to obtain data as to obstructions, strictures, resistances, and other deformities and deficiencies in the urinary tract. Other data may be garnered from examination through use of this technique.

Accordingly, it is a first object of the present invention to provide a body cavity probe with everting tube.

It is a further object of the present invention to provide such a device having a flexible insertion device and a clear barrier.

It is a further object of the present invention to provide such a device wherein an accessory channel may be provided.

It is a further object of the present invention to provide such a device which may be used in carrying out a urodynamics application.

These and other objects, aspects and features of the present invention will be better understood from the following detailed description of the preferred embodiments when read in conjunction with the appended drawing figures.

BRIEF DESCRIPTION OF THE DRAWINGS

FIG. 4 shows a cross-sectional view through a second embodiment of the present invention.

FIG. 5 shows a cross-sectional view of the embodiment of FIG. 4 in a different orientation.

FIG. 6 shows a front view of the orientation of FIG. 5.

FIG. 7 shows a cross-sectional view through a further embodiment of the present invention.

SPECIFIC DESCRIPTION OF THE PREFERRED EMBODIMENTS

Figure 1:
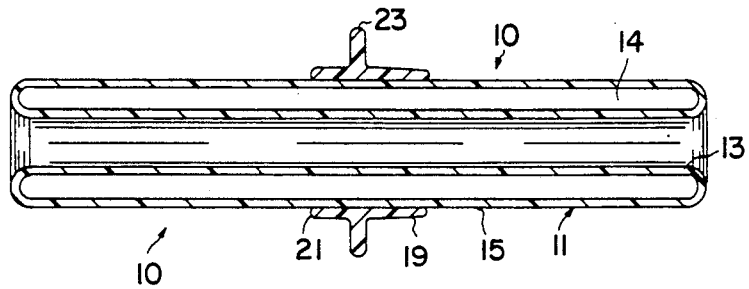
FIG. 1 shows a cross-sectional view through a first embodiment of the present invention.
Figure 2:
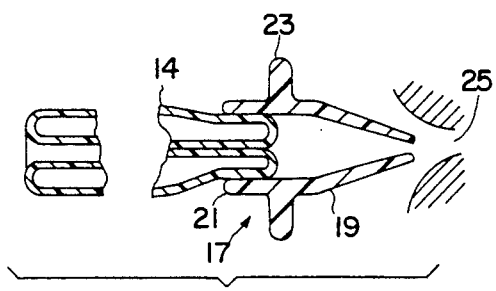
FIG. 2 shows a portion of the structure of FIG. 1 in a different orientation.
Figure 3:
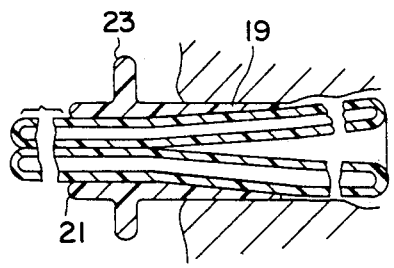
FIG. 3 shows a portion of the structure of FIG. 1 in a further orientation.

With reference first to FIGS. 1-3, a first embodiment of the present invention is shown. As seen in FIG. 1, the inventive device 10 includes an elongated tube 11 including an inner wall 13 and an outer wall 15 which form a continuous elongated annulus designed to allow everting, that is, rotation of the walls in circular fashion so that the entirety of the tube 11 may advance in one direction or another.

As further seen in FIG. 1, mounted on the outer wall 15 of the tube 11 is a flexible introduction device generally designated by the reference numeral 17. The flexible introduction device 17 includes a rearward-facing portion 21 fixedly attached to the outer wall 15 of the tube 11, a radially outwardly-extending projection 23 designed to be gripped by the user, and forward-facing portion 19 connected to the rearwardly-facing portion 21 and the radially outwardly-extending projection 23, but not attached to the wall 15 of the tube 11.

The forward-facing portion 19 is not fixedly-connected to the wall 15 of the tube 11 so that the tube 11 may be everted to a position as seen in FIG. 2 wherein the flexible introduction device 17 is forward of the remaining outer wall 15 with the forward-facing portion 19 exposed outwardly therefrom. In this position, the forward-facing portion 19 may be inserted into a body orifice such as, for example, the anus, to facilitate easy insertion of the device 10 into a body cavity.

As seen in FIG. 2, in the relaxed position of the forward-facing portion 19, the forward-facing portion 19 tapers in the forward direction so that its terminus defines an extremely small opening 25. This opening is intentionally made much smaller than the outer diameter of the walls 15 to facilitate easy insertion of the flexible introduction device 17 into a body orifice to thereby facilitate the easy introduction of the device 10 into the associated body cavity.

As should be understood with particular reference to FIG. 3, with the flexible introduction device 17 having been used in inserting the device 10 into the body cavity through insertion of the forward-facing portion 19 of the flexible introduction device 17 into the body orifice, the fluid pressure in the chamber 14 defined between the walls 13 and 15 will be sufficiently high enough to cause the forward-facing portion 19 of the flexible introduction device 17 to be stretched to a position wherein the configuration of the forward-facing portion 19 is generally cylindrical as best seen in FIGS. 1 and 3.

In the preferred mode of operation of the invention shown in FIGS. 1-3, the everting tube 11 is oriented with respect to the flexible introduction device 17 in the position shown in FIG. 2, thereafter, the forward-facing portion 19 is inserted into a body orifice such, for example, the anus, whereupon the tube 11 is everted to the position shown in FIG. 3 by introducing and advancing in frictional engagement with the inner walls 13 a viewing device or other appliance with the forward-facing portion 19 of the flexible introduction device 17 being maintained in a stationary position while the inner walls 13 of the tube 11 are transposed in a forward direction to cause insertion of the tube 11 within the body cavity, in this case the large intestine or colon.

Reference is now made to FIGS. 4, 5 and 6 which show a second embodiment of the present invention. In FIGS. 4-6, as compared to FIGS. 1-3, like elements will be described using like primed reference numerals.

With reference first to FIG. 4 it is seen that the device 10' includes an everting tube 11' having an inner wall 13' and an outer wall 15' defining therebetween an internal chamber 14'. Furthermore, the tube 11' has attached thereto, in the same manner as in the embodiment of FIGS. 1-3, a flexible introduction device 17' having a rearward-facing portion 21', a radially outwardly-extending projection 23' and a forward-facing portion 19'.

The embodiment of FIGS. 4-6 differs from the embodiment of FIGS. 1-3 as including a clear barrier device 27 which is attached within the space 16 defined within the walls 13' by virtue of sealing attachment means 29 which may comprise any suitable attachment device which maintains the integrity of the chamber 14' while fixedly attaching the clear barrier device 27 in the position shown.

As may be seen from comparison of FIGS. 4 and 5, when the tube 11' is everted, through insertion and advancement of a viewing device within and frictionally engaging the walls 13', the clear barrier device 27 may change its apparent location by virtue of the eversion of the tube 11' inner walls 13' with respect to the stationary flexible introduction device 17' so that at maximum insertion of the device 10', the clear barrier device 27 may assume the position shown in FIG. 5 as forward as it can go.

In the position of the clear barrier device 27 seen in FIG. 5, the above described viewing device may allow viewing of the internal walls and other structure of the body cavity in which the device 10' has been inserted through the clear barrier device 27 while the seals 29 prevent body fluids from entering into the chamber 16 where the viewing device is contained. In this way, viewing of internal body cavities may be accomplished without danger of the spreading of diseases carried thereby.

In a further aspect of the embodiment of FIGS. 4-6, an accessory channel 31 may be provided on the outer wall 15' of the tube 11'. The channel 31 may be in the position shown in FIG. 4, partially on the inner walls 13' and partially on the outer walls 15'. After the tube 11' has been everted to its maximum degree of insertion as seen in FIG. 5, the flexible accessory channel 31 is totally on the outer wall 15' of the tube 11', thereby allowing insertion of other instruments, as desired, into the body cavity through the inlet port 33 and thereafter out the outlet port 35 of the accessory channel 31.

Figure 8:
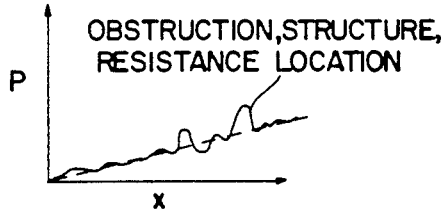
FIG. 8 shows a graph of data obtained through the use of the device of FIG. 7.
Figure 9:
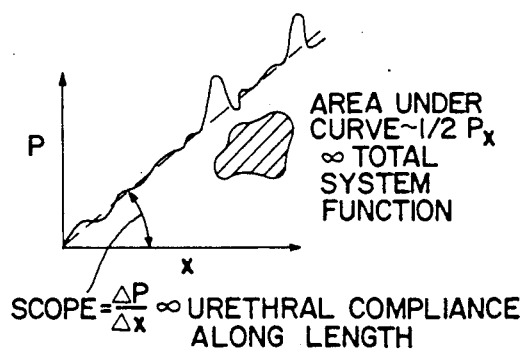
FIG. 9 shows a further graph of data obtained through the use of the device of FIG. 7.

With reference, now, to FIGS. 7, 8 and 9, a further embodiment of the present invention will be described.

With reference, first, to FIG. 7, it is seen that a device 50 includes an everting tube 51 having inner walls 53 and outer walls 55 defining a chamber 54 therebetween and a passageway 56 therethrough.

The outer wall 55 has incorporated therein a fitting 57 having a port 59 connected to a pressure transducer 61 which provides a voltage output on conductors 63 and 65. The outer walls 55 of the tube 51 are also coupled to a syringe 67, in the embodiment shown, which includes a chamber 69, the volume of which may be altered by virtue of the plunger 71 having a head 73 with outer walls 75 designed to ride in sealed relation to the inner walls 72 of the syringe 67. As should be understood from FIG. 7, when the plunger 71 is reciprocated in the right-hand direction in the Figure, fluid within the chamber 69 will be pumped therefrom into the chamber 54 defined within the tube 51 to thereby cause the tube 51 to evert and extend in the right-hand direction.

In the operation of the device 50, the tube 51 may be inserted into the entry to a body cavity such as the urethral opening and by application of pressure on the plunger 71, which pressure may vary to maintain constant speed of tube 51 advancement due to strictures, obstructions or other resistances, the tube 51 may be advanced within the urethra at a constant rate of speed. Of course, the syringe 67 may be replaced with any suitable constant flow source.

Applicant has found that as the tube 51 is advanced under constant flow, a graph of the back pressure as sensed by the pressure transducer 61 as a function of time and therefore displacement gives information about the condition of the interior of the urethra. Pressure peaks caused by back pressures indicate strictures, obstructions, or resistances. The curve of the slope is related to urethral compliance. The area under the curve is proportional to urinary tract efficiency. Thus, FIG. 8 shows a first curve which indicates several obstructions, strictures, or resistance locations with the X dimension on the curve being the distance of insertion of the end of the tube 51. FIG. 9 shows a further example of a curve showing distance of insertion of the tube 51 and pressure. As shown in FIG. 9, the area under the curve is proportional to total system function with the general slope of the curve being related to urethral compliance along the length thereof.

As such, an invention has been disclosed in terms of preferred embodiments thereof which fulfill each and every one of the objects of the invention as set forth hereinabove and which provide a new and improved body cavity probe with everting tube which is of great utility and usefulness in its environment of contemplated use. Of course, various changes, modifications, and alterations in the teachings of the present invention may be contemplated by those skilled in the art without departing from the intended spirit and scope of the present invention. As such, it is intended that the present invention only be limited by the terms of the appended claims.

We claim:

1. In an everting tube having an inner wall and an outer wall which together form a continuous elongated annular cross-section, said inner wall and outer wall defining therebetween a chamber, said inner wall surrounding an elongated open space, the improvement comprising a flexible introduction device having a rear portion and a forward portion, said rear portion having an inner surface affixed to said tube outer wall, said forward portion having a truncated conical section with an inner surface unconnected to said outer wall, said section being continuous and expansible, said device section being insertable into a body cavity orifice whereupon said tube may be everted into said body cavity through said device with said section expanding to allow said tube to evert therethrough.

2. The invention of claim 1, further including an accessory channel having an inlet and outlet and mounted on said outer wall, said accessory channel allowing access to said body cavity around said tube.

3. The invention of claim 1, wherein said flexible introduction device includes an outwardly extending gripping projection.

4. In an everting tube having an inner wall and an outer wall which together form a continuous elongated annular cross-section, said inner wall and outer wall defining therebetween a chamber, said inner wall surrounding an elongated open space, the improvement comprising a clear barrier device sealingly connected to said inner wall in said open space, whereby when said tube is everted into a body cavity through insertion of a viewing instrument into said open space and advancement thereof in frictional engagement with said inner wall, said viewing instrument may be used to view said body cavity through said clear barrier device while isolating said instrument from said body cavity.

5. The invention of claim 4, further including an accessory channel having an inlet and outlet and mounted on said outer wall, said accessory channel allowing access to said body cavity around said tube.

* * * * *